(12) United States Patent
Ishibashi et al.

(10) Patent No.: US 7,922,324 B2
(45) Date of Patent: Apr. 12, 2011

(54) SYNTHETIC RESIN LENS AND EYE LENS ARTICLE THEREOF

(75) Inventors: Fumio Ishibashi, Osaka (JP); Jindai Yamaguchi, Osaka (JP); Keishi Yoshikawa, Osaka (JP)

(73) Assignee: Yamamoto Kogaku Co., Ltd., Osaka (JP)

(*) Notice: Subject to any disclaimer, the term of this patent is extended or adjusted under 35 U.S.C. 154(b) by 7 days.

(21) Appl. No.: 12/475,851

(22) Filed: Jun. 1, 2009

(65) Prior Publication Data

US 2009/0296040 A1 Dec. 3, 2009

(30) Foreign Application Priority Data

May 30, 2008 (JP) ................................ 2008-142658

(51) Int. Cl.
*G02C 7/10* (2006.01)
(52) U.S. Cl. ........................................ 351/163; 351/159
(58) Field of Classification Search .................... 351/41, 351/159, 163–176; 359/335, 356
See application file for complete search history.

(56) References Cited

U.S. PATENT DOCUMENTS

| 3,104,176 A | 9/1963 | Hovey |
| 3,112,490 A | 12/1963 | Malcolm, Jr. |
| 5,018,223 A | 5/1991 | Dawson et al. |
| 5,428,411 A * | 6/1995 | Kopfer .............................. 351/62 |
| 7,349,151 B2 * | 3/2008 | Wu et al. ........................ 359/359 |
| 2004/0058094 A1 | 3/2004 | Hones |
| 2004/0145700 A1 * | 7/2004 | Miniutti et al. ................ 351/159 |
| 2009/0281234 A1 * | 11/2009 | Ando ............................. 524/577 |
| 2010/0009172 A1 * | 1/2010 | Morikawa et al. ............. 428/328 |

FOREIGN PATENT DOCUMENTS

| EP | 0679614 A1 | 11/1995 |
| EP | 1661534 A2 | 5/2006 |
| EP | 1935386 A1 | 6/2008 |
| JP | 2004-292754 A | 10/2004 |
| WO | 99/27397 A | 6/1999 |

OTHER PUBLICATIONS

PPG: "CR-39TM Product Bulletin", Apr. 20, 2006.
European Search Report for EP 09 16 1481 dated Sep. 3, 2009.

* cited by examiner

*Primary Examiner* — Darryl J Collins
(74) *Attorney, Agent, or Firm* — Heslin Rothenberg Farley & Mesiti P.C.

(57) ABSTRACT

The synthetic resin lens has a function to generate heat by selectively absorbing infrared rays with wavelengths of 780 to 3000 nm. The synthetic resin lens includes an infrared absorber. Selective absorption of infrared rays allows the synthetic resin lens itself to generate heat and thus the lens of the present invention has the same function as being electrically heated to prevent fogging.

7 Claims, 5 Drawing Sheets

SYNTHETIC RESIN LENS AND EYE LENS ARTICLE THEREOF

TECHNICAL FIELD OF THE INVENTION

The present invention relates to a synthetic resin lens having a function of generating heat and an eye lens article using the synthetic resin lens. Particularly, the present invention relates to protective goggles and protective glasses in which the resin lens is fitted for the purpose of preventing glare by direct light or reflected light and protecting a wearer's eyes from wind, snow, rain, seawater, water, sand, chemicals, or foreign substance in the fields of sports such as skiing, snowboarding, ice skating, yachting, boating, biking, motorcycling and the like and in the fields of industries such as ordinary manufacturing, architecture and civil engineering, firefighting and the like, and in ordinary outdoor life.

BACKGROUND OF THE INVENTION

Lenses of goggles used in skiing and the like are cooled by an outside air. The inside of the goggles is often filled with air which is warmer and more humid than the outside air due to heat emission from a wearer's body The goggles' role to prevent snow and wind from entering inside ends up with loss of air permeability. Further, if direct sunlight impinges on the goggles when the wearer is sweating, the sweat is evaporated to accelerate the above-mentioned tendency.

Under these circumstances, when the warm air generated within the goggles touches the lenses of the goggles cooled by the outside air, the lenses become fogged.

Therefore, as a method of preventing a lens surface from fogging, for example, Japanese Unexamined Patent Publication No.2004-292754 already discloses a method of providing a coating having hydrophilicity or a water-absorbing property on a lens surface, or a method of modifying the property of a lens surface.

Further, as another method of preventing a lens surface from fogging, for example, Japanese Unexamined Patent Publication No. 53-92593 discloses a method of warming up the entire lens by use of electricity.

SUMMARY OF THE INVENTION

However, even a lens, the surface of which has been treated for preventing fogging with a coating having hydrophilicity or a water-absorbing property or by modifying the property as described above, has a problem that fogging still develops on a lens surface when moisture is saturated.

Further, in the method of electrically warming up the entire lens as described above, since a power source (mostly a battery) lasts limitedly, an effect of preventing fogging is impaired when the power has been all consumed. Another problem is that, since a lens used for goggles requires flexibility, kinds of such flexible materials which generate heat are limited and material cost becomes high.

It is hence an object of the present invention to provide a synthetic resin lens in which the lens itself generates heat by selectively absorbing infrared rays and obtains the same effect as being warmed up by use of electricity.

It is another object of the present invention to provide an eye lens article using the above synthetic lens, such as goggles, sunglasses, a shield and the like, with which infrared rays are cut to 60% or less and an amount of infrared radiation passing through goggles, sunglasses or a shield and reaching a wearer's body is reduced, and in which synergistic effects of preventing a temperature rise within a goggle body and/or giving a feeling of coolness to a wearer of sunglasses and a shield can be expected.

In order to achieve the above-mentioned objects, the synthetic resin lens of the present invention is imparted a function of generating heat by selectively absorbing infrared rays with wavelengths of 780 to 3000 nanometers (nm).

Furthermore, in the synthetic resin lens of the present invention, a spectral transmittance of the infrared rays with wavelengths of 1000 to 1200 nm is 60% or less.

The synthetic resin lens of the present invention includes an infrared absorber by blending, coating or vapor-depositing.

Furthermore, the synthetic resin lens of the present invention is made of a synthetic resin having water absorption of less than 0.1%.

Further, the synthetic resin lens of the present invention includes a synthetic resin having water absorption of less than 0.1% by bonding.

The eye lens article of the present invention is produced by using any one of the foregoing synthetic resin lenses.

Furthermore, the eye lens article of the present invention is produced by using any one of the foregoing synthetic resin lenses in a lens member having a double structure (a double structural lens member) in which an outer lens and an inner lens are joined together with a space therebetween.

Further, the eye lens article of the present invention is produced by using any one of the foregoing synthetic resin lenses as the outer lens of the double structural lens member in which the outer lens and the inner lens are joined together with a space therebetween and using a lens to reflect infrared rays with wavelengths of 780 to 3000 nm as the inner lens of the lens member.

Furthermore, the eye lens article of the present invention may be such as goggles, sunglasses, shields and the like.

Since the synthetic resin lens of the present invention is constituted as stated above, the lens itself develops heat by selectively absorbing infrared rays. Therefore, the lens can be prevented from being cooled, and due to heating-up of the lens itself the lens can have the same effect as being electrically warmed up.

Furthermore, in the eye lens article of the present invention such as the goggles, the sunglasses, the shield and the like, infrared rays can be cut to 60% or less and the amount of infrared radiation, which passes through the goggles, the sunglasses or the shield and reaches a wearer's body, is also reduced, and thus a rise in temperature of a wearer's skin can be prevented and simultaneously evaporation of the wearer's sweat can be reduced. Therefore, there may be synergistic effects that the goggles prevent a rise in temperature within the goggle body, and the sunglasses or the shields make a wearer feel cool.

DESCRIPTION OF SPECIFIC EMBODIMENT

Figure 1:
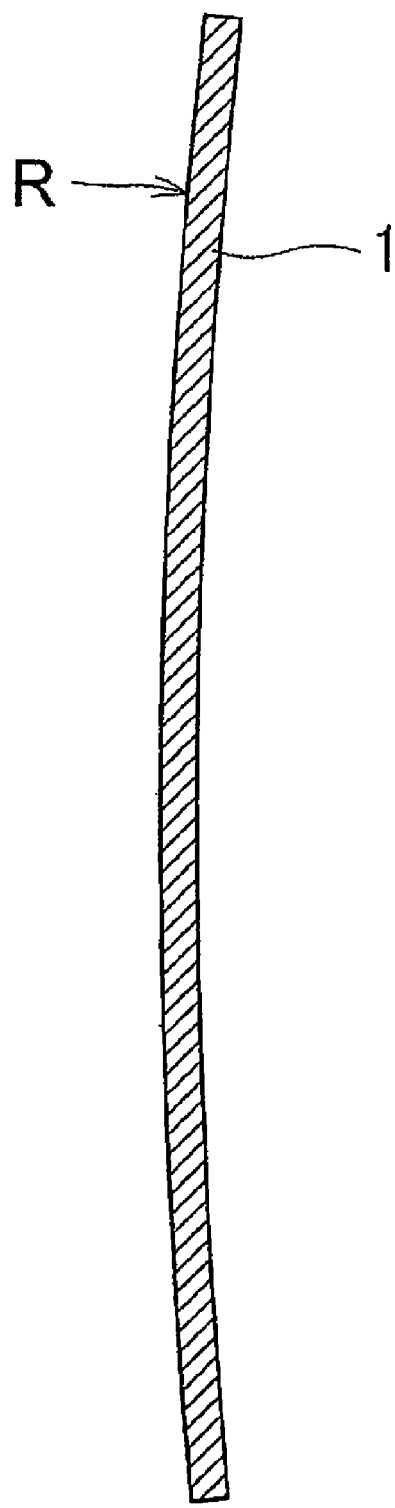
FIG. 1 is a sectional view showing an embodiment of a lens structure of an eye lens article according to the present invention.

Hereinafter, the preferred embodiments for carrying out a synthetic resin lens of the present invention will be described in detail.

The synthetic resin lens of the present invention has a function to generate heat by selectively absorbing infrared rays with wavelengths of 780 to 3000 nm.

Furthermore, the synthetic resin lens of the present invention includes an infrared absorber which has an absorption peak on a short wavelength side of 1000 to 1200 nm in near-infrared rays of 780 to 3000 nm in wavelength and cuts infrared rays with wavelengths of about 700 to about 1600 nm. The infrared absorber may be included in the lens by blending, coating or vapor-depositing.

In the synthetic resin lens of the present invention, a spectral transmittance of the infrared rays with wavelengths of 1000 to 1200 nm is 60% or less. The transmittance of the infrared rays larger than 60% is not preferable because the lens with such transmittance develops less heat.

The foregoing infrared absorber may be selected from organic compounds such as phthalocyanine-based compounds, polymethyl-based compounds, cyanine-based compounds, quinone-based compounds, diimmonium-based compounds, anthraquinone-based compounds, azo-based compounds, oxazine-based compounds, coumarin-based compounds, benzopyrylium-based compounds, aminium-based compounds, cyanine dye-based compounds, squarylium dye, methine-based dyes, quinoneimine-based dyes, quinonediimine-based dyes and the like.

When blending the infrared absorber in a lens base to produce the synthetic resin lens of the present invention, the proper amount of the infrared absorber to be blended is 0.0001 to 0.5 part by weight with respect to 100 parts by weight of the synthetic resin, but 0.001 to 0.2 part by weight is preferable in order to reliably reduce the transmittance of the infrared rays to 60% or less.

When coating the infrared absorber on a lens base to produce the synthetic resin lens of the present invention, the amount of the infrared absorber to be mixed is 0.001 to 5 parts by weight with respect to 100 parts by weight of a synthetic resin and the resultant mixture is coated on the lens base to a thickness of 0.001 to 0.5 mm.

When the thickness of coating is smaller than this range, the transmittance of the infrared rays increases and a sufficient effect of generating heat is not achieved, while when the thickness of coating is larger than this range, it becomes difficult to select production conditions or coating film materials for attaining adhesive strength between the coating and the synthetic resin lens base. Further, it becomes difficult to attain an optical smooth surface. Therefore, the thickness of coating is preferably about 0.003 to about 0.1 mm.

When depositing the infrared absorber over a lens base surface by vapor deposition to produce the synthetic resin lens of the present invention, it is proper that the thickness of the infrared absorber to be deposited on a formed lens base of synthetic resin is 0.01 to 50 μm, and preferably about 0.3 to about 10 μm. When the thickness of the vapor deposition is thinner than 0.01 μm, an adequate effect of absorbing infrared rays is not achieved, on the other hand, when the thickness is larger than 50 μm, a vapor deposition film is deformed or distorted.

The synthetic resin lens of the present invention is suitable to have a spherical shape and a radius of curvature of 50 to 600 mm, and a radius of curvature of 70 to 130 mm is preferable. Not only a lens having a single spherical surface but also a lens having an aspheric surface such as a toroidal surface or a sculptured surface may be adapted. These synthetic resin lenses may be formed by forcibly processing a flat plate of 0.3 to 4 mm in thickness into a spherical or aspheric figure by heat or may be formed by molding synthetic rein material directly into a spherical or aspheric form.

The synthetic resin lens of the present invention preferably has water absorption of 0.5% or less, preferably less than 0.1%, when a double structural lens member is employed. The synthetic resin lens of the present invention may be formed by bonding a synthetic resin having water absorption of less than 0.1% with a lens base. Water absorption of the lens less than 0.1% may allow less moisture to penetrate into a space between an outer lens and an inner lens of the double structural lens member, as described below.

Materials of the synthetic resin lens of the present invention include, for example, a polycarbonate resin (water absorption 0.4%), nylon (water absorption 2.9%), cellulose propionate (water absorption 3.0%), urethane (water absorption 0.3%), PMMA (water absorption 2%), a special acrylic-based resin (water absorption 1.2%), and a norbomene-based resin (water absorption 0.4%). Lens materials having a low water-absorbing property include, for example, an AS resin (water absorption 0.1%) and an EVA resin (water absorption 0.1%), and lens material having a lower water-absorbing property include, for example, cyclic olefin-based polymers (water absorption 0.01% or less) and cyclopolyolefin polymer (water absorption 0.01% or less). The water absorption referred to herein is determined according to ASTM Standard "ASTM D570".

Next, the eye lens article of the present invention is produced by using the above mentioned synthetic resin lens and is applied to goggles, sunglasses or the like which are usually used outdoors. Furthermore, the synthetic resin lens absorbing infrared rays also functions as heat shielding, and thus the eye lens article of the present invention can also be applied to a shield.

Figure 2:
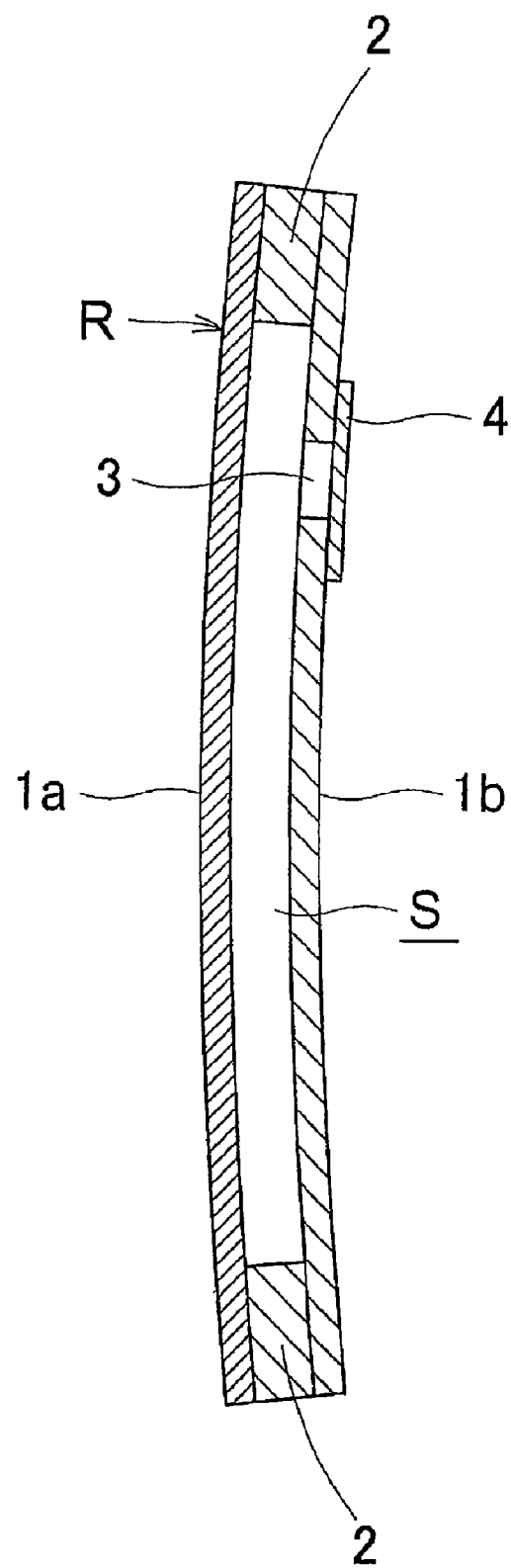
FIG. 2 is a sectional view showing another embodiment of a lens structure of an eye lens article according to the present invention.
Figure 3:
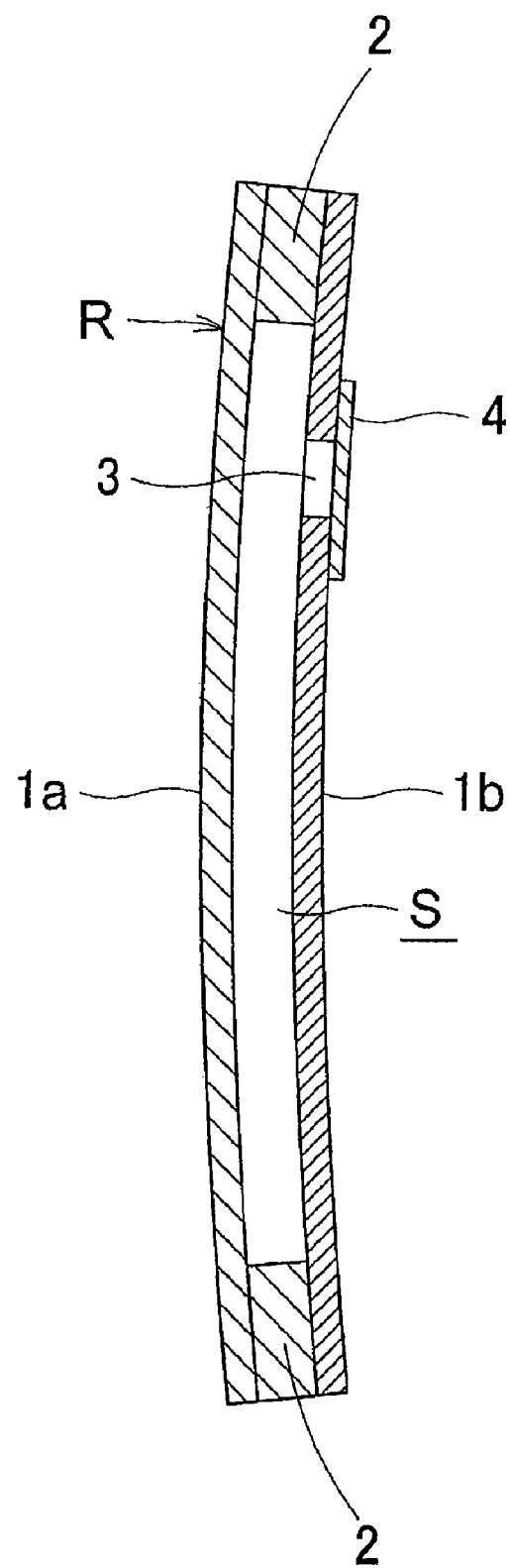
FIG. 3 is a sectional view showing a further embodiment of a lens structure of an eye lens article according to the present invention.
Figure 4:
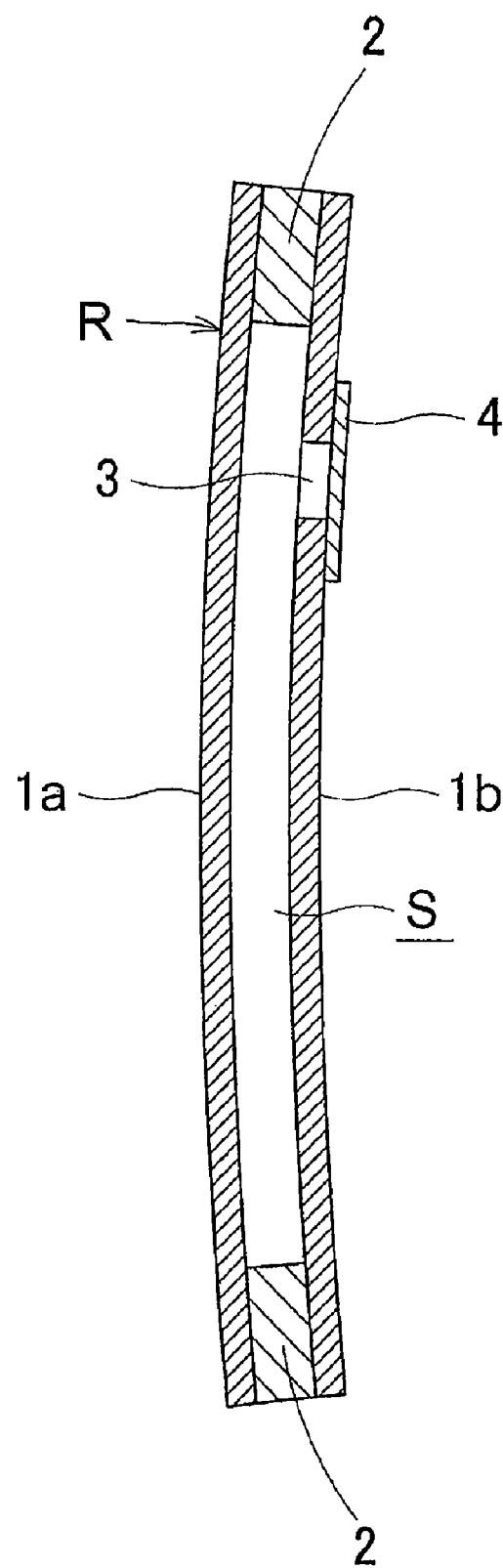
FIG. 4 is a sectional view showing a further embodiment of a lens structure of an eye lens article according to the present invention.

Here are some specific embodiments. The eye lens article of the present invention may employ the synthetic resin lens in the lens member R of single structure having a single lens 1, as shown in FIG. 1, or it may employ the synthetic resin lens in the double structural lens member R (the double lens member) having an outer lens 1*a* and an inner lens 1*b* joined together with a space S therebetween, as shown in FIGS. 2 to 4. In FIG. 2, the synthetic resin lens is employed as the outer lens 1*a* of the lens member R; in FIG. 3, the synthetic resin lens is employed as the inner lens 1*b* of the lens member R; and in FIG. 4, the synthetic resin lens is employed as both the outer lens 1*a* and the inner lens 1*b*.

If an eye lens article has a double-structural lens member of a synthetic resin, since some synthetic resins have a water-absorbing property, moisture may pass through an outer lens and an inner lens of the double-structural lens member and may penetrate into a space between the two lenses. When a certain amount of moisture penetrates into the space, the lens member starts to fog. However, in the eye lens article of the present invention, moisture penetration into the space S can be inhibited by forming at least one of the outer lens 1*a* and the inner lens 1*b* as stated above. Specifically, at least one of the lenses is made of the synthetic resin having water absorption of less than 0.5%, or preferably less than 0.1%. Furthermore, at least one of the lenses may be formed by bonding or attaching by insert molding a synthetic resin having a low water-absorbing property, more specifically, a water absorption of less than 0.5%, or preferably less than 0.1%, to a synthetic resin lens base.

In the eye lens article of the present invention, the outer lens 1a may be the foregoing synthetic resin lens, while the inner lens 1b may be a lens which reflects infrared rays with wavelengths of 780 to 3000 nm. In this structure, the infrared rays once reflected by the inner lens 1b are absorbed again by the outer lens 1a, which preferably enhances a rise in temperature of the lens member R.

The present invention will be described in more detail in conjunction with some examples.

EXAMPLE 1

Ski goggles (double lens) were prepared with the synthetic resin lens of the present invention.

Figure 5:
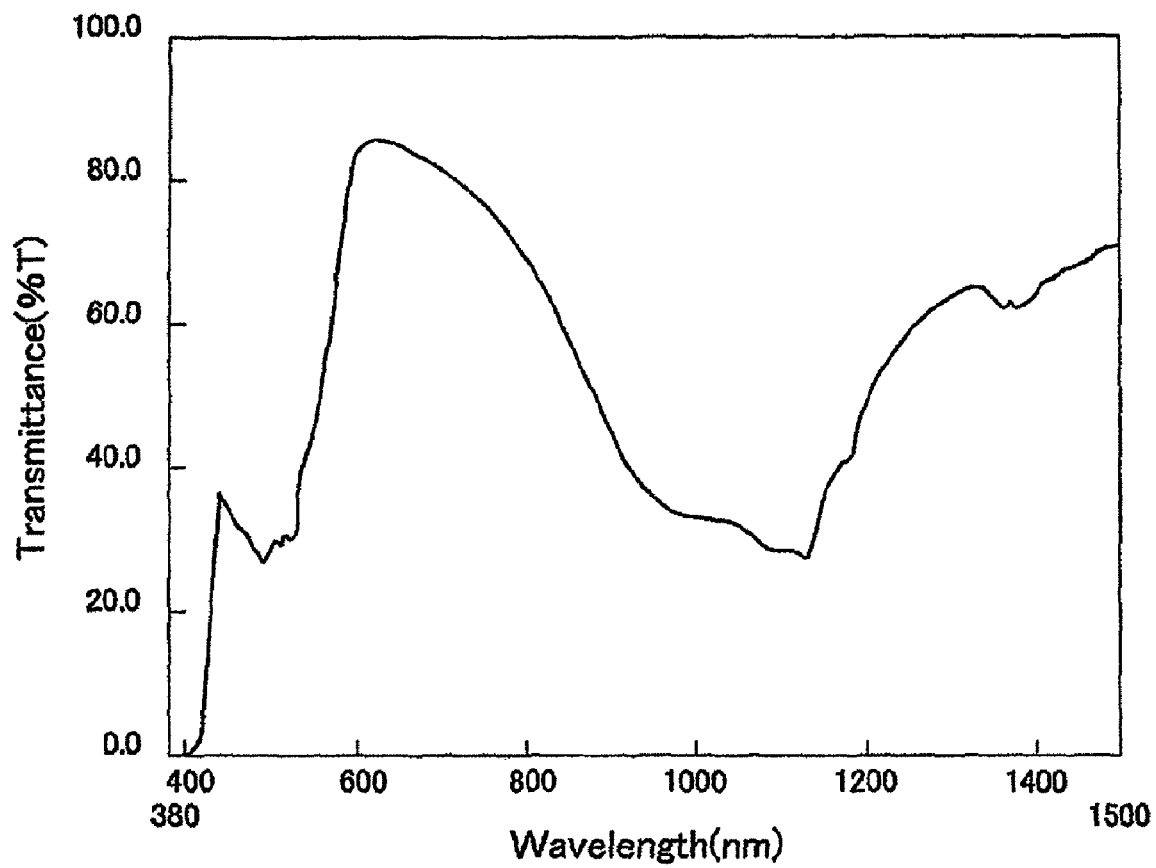
FIG. 5 is a graph showing a spectral transmittance of a synthetic resin lens of the present invention.

An outer lens 1a of the double lens member of the ski goggles was prepared as follows: 0.005 part by weight of an infrared absorber (IRG-022 produced by Nippon Kayaku Co., Ltd.) was mixed in 100 parts by weight of a polycarbonate resin S-2000 produced by Mitsubishi Gas Chemical Company, Inc.; in this mixture, 0.03 part by weight of a red dye (MLP Red-2, produced by Mitsui Chemicals, Inc.) having a function of absorbing blue or green was mixed for adjusting the transparency; the resultant mixture was extruded to obtain a 0.3 mm orangey sheet; to this sheet, a transparent sheet of 0.5 mm in thickness made of cyclopolyolefin resin having water absorption of 0.01% or less, produced by Japan Zeon Corporation, was bonded to obtain a multilayered sheet having a thickness of about 0.8 mm. The transmittance of visible light of this resultant multilayered sheet was about 50%, and the spectral transmittance had a lower limit in a near-infrared region of 1000 to 1200 nm, which was about 28% including thereabout, as shown in FIG. 5. The process of the sheet to shape the outer lens 1a of the double lens member follows.

An inner lens 1b of the double lens member of the ski goggles was obtained by laminating a 0.3 mm transparent polycarbonate resin sheet and a 0.5 mm transparent sheet of cyclopolyolefin resin by bonding, the 0.5 mm transparent sheet being produced by Japan Zeon Corporation, coating a surface on the polycarbonate side of the resultant laminated sheet with a film having a water-absorbing property and an effect of preventing fogging, and then punching the resultant coated sheet to have a shaped lens.

The outer lens 1a and the inner lens 1b formed as stated above were respectively bonded to a gasket 2, which was mainly made of CR-based rubber, with a double-sided tape to be fixed together and form a space S of about 2 mm. The inner lens 1b was provided with a hole 3 for adjusting a pressure and a seal 4 having moisture permeability was bonded to cover the pressure adjusting hole 3 in order to prevent moisture from entering. A double lens member was then obtained.

After fabricating the double lens member as stated above, the environment of a thermo-hygrostat bath was kept at 30° C./relative humidity 90% and the double lens member was put in the bath for 24 hours. Thereafter, the double lens member was taken out of the thermo-hygrostat bath and fitted in the goggle frame to form a pair of ski goggles.

The ski goggles of the eye lens article of the present invention constituted as above were irradiated with pseudo sunlight with irradiation intensity of 50000 1x under the environment of an outside air temperature of −5° C., and consequently a temperature of the outer lens 1a rose to 15° C. Since a dew point temperature of the space S in the double lens member at that time was 12° C., the lens member R did not fog.

The same irradiation with pseudo sunlight was conducted with respect to ski goggles with a double lens member having the almost same color but not having a function of absorbing infrared rays, the temperature of the lens rose only to 10° C. The dew point temperature of the space in the double lens member at that time was 12° C., and the lens gradually started to fog.

EXAMPLE 2

As an eye lens article of the present invention, a pair of goggles was prepared by using the synthetic resin lens of the present invention.

A lens 1 of this pair of goggles was prepared by mixing 0.008 part by weight of an infrared absorber (NIR-IM1 produced by Nagase ChemteX Corporation) in 100 parts by weight of a polycarbonate resin S-2000 produced by Mitsubishi Gas Chemical Corporation, Inc., and molding the resultant mixture.

The molded lens 1 had a thickness of 2 mm, a radius of curvature of about 87 mm, and about 55% transmittance of visible light. The lower limit of the spectral transmittance appeared in a near-infrared region of 1000 to 1200 nm and the spectral transmittance of the lower limit and thereabout was about 30%.

This lens 1 was cut into the shape of a lens of a pair of snow goggles. A surface of the lens 1 which, in the pair of the goggles, would became facing toward a wearer's face was coated with a film provided with a water-absorbing property and having an effect of preventing fogging.

The lens 1 prepared as stated above was fitted in a goggle frame.

The pair of goggles constituted as above, i.e. the eye lens article of the present invention, was practically used in a ski ground and tested. The temperature of the lens 1 and a temperature within the goggles were measured. When tested, there was no cloud in the sky and no wind in the ski ground.

The temperature of the surface of the lens 1 rose up to 32° C. At that time, the dew point temperature within the goggles was 28° C. (30° C./relative humidity 80%). Since the surface temperature of the lens 1 was higher than the dew point temperature within the goggles, the lens 1 could remain unfogged.

A pair of goggles fitted with a lens with a similar color and no function of absorbing infrared rays was tested similarly. The surface temperature of the lens rose up to 25° C. The dew point temperature within the goggles was 28° C. (30° C./relative humidity 80%). Since the surface temperature of the lens was lower than the dew point temperature within the goggles, the lens became fogged.

EXAMPLE 3

A shield, as the eye lens article of the present invention, was prepared by using the synthetic resin lens of the present invention.

A lens 1 of the shield which was prepared by mixing 0.008 part by weight of an infrared absorber (CIR 1081 produced by Japan Carlit Co., Ltd.) in 100 parts by weight of a polycarbonate resin S-2000 produced by Mitsubishi Gas Chemical Corporation, Inc., further mixing 0.02 part by weight of a red dye (MLP Red-2, produced by Mitsui Chemicals, Inc.) having a function of absorbing blue or green for adjusting the transparency, and molding the resultant mixture to make an orangey lens.

The molded lens had a thickness of 2 mm, a radius of curvature of about 87 mm, and about 54% of a transmittance of visible light. The spectral transmittance had a lower limit in a near-infrared region of 1000 to 1200 nm and the spectral transmittance of the lower limit and thereabouts was about 22%. Subsequently, the molded lens was cut into the shape for a shield.

The shield of the eye lens article of the present invention constituted as above was irradiated with pseudo sunlight with irradiation intensity of 100000 1× under the environment of an outside air temperature of 0° C. There was no fogging on the lens 1. The surface temperature of a wearer's body rose from 35° C. to 37° C.

A shield with a lens with a similar color and no function of absorbing infrared rays was tested similarly. On the inside of the lens fogging grows gradually. On the other hand, the surface temperature of the wearer's body rose up to 39° C.

EXAMPLE 4

A pair of ski goggles (double lens), or the eye lens article of the present invention, was prepared with the synthetic resin lens of the present invention.

The lens for the double lens member of this pair of ski goggles was prepared by mixing 0.005 part by weight of an infrared absorber (IRG022 produced by Nippon Kayaku Corporation, Ltd.) in 100 parts by weight of a polycarbonate resin S-2000 produced by Mitsubishi Gas Chemical Corporation, Inc., further mixing therein 0.03 part by weight of a red dye (MLP Red-2, produced by Mitsui Chemicals, Inc.) having a function of absorbing blue or green for adjusting the transparency, and molding the resultant mixture to make an orangey lens.

The molded lens had a thickness of 2 mm, a radius of curvature of about 87 mm, and about 50% transmittance of visible light. The spectral transmittance had a lower limit in a near-infrared region of 1000 to 1200 nm and the spectral transmittance of the lower limit and thereabout was about 28%, as shown in FIG. 5.

In order to make an inner lens 1b of the double lens structure of the ski goggles, the surface to be an inner surface of the lens 1b of a 0.6 mm polycarbonate sheet was coated with a film provided with a water-absorbing property and having an effect of preventing fogging. The outer surface of the resultant sheet, in other words, the surface which would partially define a space S between an inner and an outer lens of the ski goggles, was provided with a silver mirror by vapor deposition. The resultant sheet was punched out to obtain a shaped lens.

Obtained outer and inner lenses 1a and 1b were respectively bonded to a gasket 2, which was mainly made of CR-based rubber, with a double-sided tape to be fixed together and form a space S of about 2 mm. The inner lens 1b was provided with a hole 3 for adjusting a pressure and a seal 4 having moisture permeability was bonded to cover the pressure adjusting hole 3 in order to prevent moisture from entering. A double lens member was obtained.

The environment of a thermo-hygrostat bath was kept at 30° C./relative humidity 90% and the obtained double lens member was put in the bath for 24 hours. Thereafter, the double lens member was taken out of the thermo-hygrostat bath and fitted in the goggle frame to form a pair of ski goggles.

The ski goggles of the eye lens article of the present invention constituted as above were irradiated with pseudo sunlight with irradiation intensity of 50000 1× under the environment of an outside air temperature of −5° C., and consequently a temperature of the outer lens 1a rose to 20° C. Since a dew point temperature of the space S in the double lens member at that time was 14° C., the lens member R did not fog.

The same irradiation with pseudo sunlight was conducted with respect to ski goggles with a double lens member having the almost same color but not having a function of absorbing infrared rays, the temperature of the lens rose only to 12° C. The dew point temperature of the space in the double lens member at that time was 14° C., and the lens gradually started to fog.

What is claimed is:

1. An eye lens article comprising a double structural lens member in which an outer lens and an inner lens are joined together with a space therebetween, wherein a synthetic resin lens, which includes an infrared absorber by one of blending, coating and vapor-depositing, and having a function to generate heat by selectively absorbing infrared rays with wavelengths 780 to 3000 nm, is used as the outer lens of the lens member, and a lens reflecting infrared rays with wavelengths of 780 to 3000 nm is used as the inner lens of the lens member.

2. The eye lens article according to claim 1, wherein the synthetic resin lens is made of a synthetic resin having water absorption of less than 0.1%.

3. The eye lens article according to claim 1, wherein a synthetic resin having water absorption of less than 0.1% is included in the synthetic resin lens by bonding.

4. The eye lens article according to claim 1, wherein the article is one of a pair of goggles, a pair of sunglasses and a shield.

5. The eye lens article according to claim 1, wherein, in the syntheyic resin lens, a spectral transmittance of infrared rays with wavelengths of 1000 to 1200 nm is 60% or less.

6. The eye lens article according to claim 5, wherein the synthetic resin lens is made of a synthetic resin having water absorption of less than 0.1%.

7. The eye lens article according to claim 5, wherein a synthetic resin having water absorption of less than 0.1% is included in the synthetic resin lens by bonding.

* * * * *